(12) United States Patent
Perlmutter et al.

(10) Patent No.: US 6,656,912 B2
(45) Date of Patent: Dec. 2, 2003

(54) METHODS TO TREAT α1-ANTITRYPSIN DEFICIENCY

(75) Inventors: David H. Perlmutter, St. Louis, MO (US); Nancy Marcus, St. Louis, MO (US)

(73) Assignee: Washington University in St. Louis, St. Louis, MO (US)

( * ) Notice: Subject to any disclaimer, the term of this patent is extended or adjusted under 35 U.S.C. 154(b) by 267 days.

(21) Appl. No.: 09/768,029

(22) Filed: Jan. 22, 2001

(65) Prior Publication Data

US 2002/0006909 A1 Jan. 17, 2002

Related U.S. Application Data

(60) Provisional application No. 60/177,472, filed on Jan. 21, 2000, and provisional application No. 60/177,392, filed on Jan. 20, 2000.

(51) Int. Cl.[7] ..................... A61K 31/70; A61K 31/435; C07D 221/02
(52) U.S. Cl. ........................... 514/23; 514/299; 514/42; 514/673; 546/183
(58) Field of Search ........................... 514/23, 299, 42, 514/673; 546/183

(56) References Cited

PUBLICATIONS

Sasak et al., Biochemical Journal (1985), 232(3), 759–66.*
Sasak et al.(Biochemical Journal (1985), 232(3), 759–66 (abstract sent).*
Robinson et al (Enzyme (1982), 27 (2), 99–107 (abstract sent).*
Bolmer et al., XP002170749, abstract.
Burrows et al., Proc. Natl. Acad. Sci. USA (2000) 97:1796–1801.
Gross et al., Biochem. J. (1986) 236:853–860.
Jallat et al., Protein Engineering (1986) 1(1):29–35.
Liu et al., J. Biol. Chem. (1997) 272:7946–7951.
Liu et al., J. Biol. Chem. (1999) 274:5861–5867.
Lodish et al., XPoo2170750, abstract.
Marcus and Perlmutter, Gastroenterology (2000) 118:1160.
Marcus et al., J. Biol. Chem. (2000) 275:1987–1992.
Novoradovskaya et al., The Journal of Clinical Investigation (1998) 101(12):2693–2701.
Qu et al., J. Biol. Chem. (1996) 271:22791–22795.
Rubenstein et al., Journal of Clinical Investigation (1997) 100(10):2457–2465.
Teckman et al., Am. J. Physiol–Gastro and Liver Physiol. (2000) 278:G39–G48.
Winchester et al., Glycobiology (1992) 2(3):199–210.

* cited by examiner

*Primary Examiner*—Samuel Barts
*Assistant Examiner*—Michael C. Henry
(74) *Attorney, Agent, or Firm*—Morrison & Foerster LLP

(57) ABSTRACT

Inhibitors of glucosidase, especially those related to castanospermine, are effective in preventing or ameliorating conditions such as liver damage and emphysema that are present in individuals who produce a mutant form of antitrypsin, α1-ATZ. Also effective in the method of the invention are imino sugars and their reduced forms in general as well as phenylbutyric acid. These compounds enhance the secretion of the mutant form, which retains substantial biological activity, and do not impair its degradation in the endoplasmic reticulum.

6 Claims, No Drawings

METHODS TO TREAT α1-ANTITRYPSIN DEFICIENCY

CROSS-REFERENCE TO RELATED APPLICATIONS

This application claims priority under 35 U.S.C. §119(e) to provisional application 60/177,472 filed Jan. 21, 2000 and to application 60/177,392 filed Jan. 20, 2000. The contents of these applications are incorporated herein by reference.

ACKNOWLEDGMENT OF GOVERNMENT SUPPORT

This invention was made in part using funds granted by the National Institutes of Health under contracts HL 37784 and DK 52526. The U.S. government has certain rights in this invention.

TECHNICAL FIELD

The invention relates to treatment of α1-antitrypsin (α1-AT) deficiency in individuals containing a mutant form of α1-AT exhibiting symptoms of, or at-risk for, liver damage and/or emphysema. In particular, the invention concerns the use of inhibitors of glucosidase and in some instances, of mannosidase in ameliorating these conditions.

BACKGROUND ART

The enzyme α1-antitrypsin (α1-AT) is important in maintaining the condition of lung tissue by virtue of its ability to inhibit neutrophil elastase. If this elastase inhibitor is lacking in the lungs, lung diseases such as emphysema can develop. A substantial number of individuals are deficient in this important enzyme by virtue of the presence of a mutant form of the glycoprotein, designated α1-ATZ, differing from the wild type by a single amino acid substitution. Although α1-ATZ this retains approximately 80% of the functional activity of the wild type in inhibiting neutrophil elastase, because it is misfolded and polymerized in the endoplasmic reticulum (ER) of liver cells rather than excreted into the extracellular fluid, it exerts a hepatotoxic effect, especially in infants and children, and is not available in the lungs to carry out its function. There are, however, known pathways for degradation of the mutant α1-ATZ in the ER—one involving the sequence of stable binding to calnexin, conjugation of ubiquitin to the cytoplasmic tail of the complexed calnexin and degradation of the resulting complex by the proteasome (Qu, D., et al., *J. Biol. Chem.* (1996) 271:22791–22795). There is also a ubiquitin-independent proteasomal mechanism (Teckman, J. H., et al., *Biochem J.* (1986) 236:853–860).

It is apparent that individuals having the genotype which results in the production of the mutant α1-ATZ would benefit if the secretion of this mutant form of α1-AT could be enhanced, since this mutant form does retain the desired neutrophil elastase inhibition activity. Such individuals would also benefit by any protocol which would result in the enhanced degradation of this mutant form in the ER, thus ameliorating the hepatotoxicity of the misfolded polymer. It has been shown that glucosidase and mannosidase inhibitors inhibit secretion of wild type α1-AT (Gross, V., et al, *Biochem. J.* (1986) 236:853–860). It has also been shown that a different mutant α1-AT which is retained and degraded in the ER, α1-AT$_{HONG\ KONG}$, is affected by such inhibitors in that ER degradation is accelerated by glucosidase inhibitors and delayed by mannosidase inhibitors (Liu, Y., et al., *J. Biol. Chem.* (1997) 272:7946–7951; Liu, Y., et al.,*J. Biol. Chem.* (1999) 274:5861–5867).

In general, it is understood that addition and trimming of oligosaccharide side chains are significant factors in the secretion, degradation, and transport of secretory, membrane and lyosomal glycoproteins. It is also known that transport of secretory and membrane glycoproteins from the ER to their appropriate destination depends on the interaction of the innermost glucose residue of oligosaccharide side chains with the ER molecular chaperones calnexin and calreticulin so that trimming of the oligosaccharide coupled to the asparagine residue in the peptide backbone by, for example, glucosidases I and II influence the proper folding and translocation of glycosylated proteins.

Experimental work related to the present invention has been described by applicants in Marcus, N.Y., and Perlmutter, D. H., *Gastroenterology* (2000) 118:1160 (meeting abstract entitled "Glucosidase and Mannosidase Inhibitors Mediate Increased Secretion of A1 Antitrypsin Z"; Burrows, J. A. J., et al., *Proc. Natl. Acad. Sci (USA)* (2000) 97:1796–1801 (article entitled "Chemical Chaperones Mediate Increased Secretion of Mutant alpha 1-Antitrypsin (alpha 1-AT) Z: A Potential Pharmacological Strategy for Prevention of Liver Injury and Emphysema in alpha 1-AT deficiency"); Marcus, N.Y., et al., *J. Biol. Chem.* (2000) 275:1987–1992 (article entitled "Glucosidase and Mannosidase Inhibitors Mediate Increased Secretion of Mutant alpha 1-Antitrypsin Z"); and Teckman, J. H., et al.,*Am. J. Physiol-Gastro and Liver Physiol.* (2000) 278:G39–G48 (article entitled "Role of Ubiquitin in Proteosome al Degradation of Mutant alpha 1-Antitrypsin Z in the Endoplasmic Reticulum"). The contents of these publications are incorporated herein by reference.

DISCLOSURE OF THE INVENTION

It has now been found that inhibitors of glucosidase enhance the secretion of the mutant α1-ATZ glycoprotein without impairing its degradation in the ER. Inhibitors of mannosidase I also enhance secretion of mutant α1-ATZ, but delay its degradation in the ER. Compounds which are imino sugars or reduced forms thereof, such as derivatized deoxynojirimycin, are also useful in the methods of the invention.

Thus, in one aspect, the invention is directed to treat conditions associated with α1-antitrypsin deficiency caused by the presence of mutant α1-ATZ glycoprotein which method comprises administering to a subject in need of such treatment an effective amount of an inhibitor of glucosidase so as to enhance the secretion of the mutant α1-ATZ. In another aspect, the invention relates to methods to treat hepatotoxic conditions caused by the presence of mutant α1-ATZ in the endoplasmic reticulum which method comprises administering an effective amount of a glucosidase inhibitor to a subject in need of such treatment. In still another aspect, the invention is directed to ameliorating emphysema in individuals wherein the emphysema is caused by an α1-AT deficiency due to the presence of the mutant α1-ATZ which method comprises administering to individuals in need of such treatment an effective amount of a glucosidase inhibitor or a mannosidase I inhibitor.

Also useful in the various methods of the invention set forth above are imino sugars and their reduced forms. Imino sugars include analogs of hexoses or pentoses wherein the 5 or 4 position contains amino as opposed to hydroxy.

In other aspects, the invention relates to pharmaceutical compositions containing the aforementioned inhibitors and compounds.

Modes of Carrying Out the Invention

Clinical studies have shown that only partial correction is needed for prevention of both liver and lung injury in patients having α1-antitrypsin deficiency. See Wu, Y., et al., *Proc. Natl. Acad. Sci. (PNAS) U.S.A.* (1994) 91:9014–9018; Campbell, E. J., et al., *J. Clin. Invest.* (1999)104:337–344). Thus, the ability of glucosidase inhibitors and mannosidase I inhibitors to enhance the secretion of α1-ATZ, which retains significant portion of the activity of the wild type α1-AT, make such compounds effective medications for treating the clinical symptoms associated with deficiency caused by the presence of α1-ATZ. Secretion can also be enhanced by 4-phenylbutyric acid (PBA).

Suitable subjects are those individuals whose genetic composition results in the production of the mutant form of α1-antitrypsin, α1-ATZ. These individuals can be determined by known methods, such as genetic typing and immunological tests. If subjects present with symptoms such as emphysema or liver malfunction, determination of whether or not the individual produces α1-ATZ is straightforward, routine, and readily performed. For use of the method of the invention in preventing the onset of such conditions, a suitable screening program would be desirable.

As used herein, "treat" or "treatment" includes ameliorating the effects of a condition already present as well as preventing the onset of symptomologies. Thus, "treatment" includes both therapeutic and prophylactic protocols.

The active ingredients in the compositions used in the methods of the invention are preferably glucosidase inhibitors, since these inhibitors both enhance the secretion of α1-ATZ and enhance its degradation in the ER. Such inhibitors include castanospermine (CST), which is a polyhydroxy alkaloid isolated from plant sources known to inhibit enzymatic glycoside hydrolysis, N-butyldeoxynojirimycin (BDNJ), N-nonyl DNJ (NDNJ), N-hexyl DNJ (HDNJ), and N-methyldeoxynojirimycin (MDNJ). These compounds are reduction products of imino sugars; it is understood that imino sugars and their reduction products are useful in the invention methods. Suitable mannosidase I inhibitors include deoxymannojirimycin (DMJ), which inhibits both mannosidase I and mannosidase II, and kifunensine (KIF), which inhibits mannosidase I. Other known inhibitors of glucosidase and mannosidase I can also be used.

Deoxynojirimycin is the reduction product of an imino sugar; an alternative name for deoxynojirimycin is 5-amino-1,5-dideoxy glucopyranose.

In addition to use of glucosidase or mannosidase inhibitors per se, it appears that, imino sugars or their reduction products generally are useful in the methods of the invention. Additional imino sugar compounds similar to CST are disclosed in Jacob, G. S., et al., *Cur. Opin. Struct. Biol.* (1995) 5:605–611; Winchester, B., et al., *Glycobiol* (1992) 2:199–210. While it appears that many imino sugars and their reduction products inhibit hydrolysis of glycose moieties, applicants wish not to be bound by any particular theory of the mechanism by which these imino sugars are able to exert their desirable effects on α1-ATZ retention in the ER.

The compositions of the invention are preferably administered systemically. For systemic use, the compounds herein are formulated for parenteral (e.g., intravenous, subcutaneous, intramuscular, intraperitoneal, intranasal or transdermal) or enteral (e.g., oral or rectal) delivery according to conventional methods. In general, because the disorders associated with the presence of α1-ATZ are chronic rather than acute, continued administration will generally be necessary. Therefore, preferably, administration will be by an enteral route, most preferably oral. Intravenous administration, less preferred, can be by a series of injections or by continuous infusion over an extended period. Administration by injection or other routes of discretely spaced administration can be performed at intervals ranging from weekly to once to three times daily. Alternatively, the compounds disclosed herein may be administered in a cyclical manner (administration of compound; followed by no administration; followed by administration of compound, and the like). Mixture of active compounds may also be used.

In general, pharmaceutical formulations will include a compound of the present invention in combination with a pharmaceutically acceptable vehicle, such as saline, buffered saline, 5% dextrose in water, borate-buffered saline containing trace metals or the like. Formulations may further include one or more excipients, preservatives, solubilizers, buffering agents, albumin to prevent protein loss on vial surfaces, lubricants, fillers, stabilizers, etc. Methods of formulation are well known in the art and are disclosed, for example, in *Remington's Pharmaceutical Sciences*, latest edition, Mack Publishing Co., Easton Pa., which is incorporated herein by reference. Pharmaceutical compositions for use within the present invention can be in the form of sterile, non-pyrogenic liquid solutions or suspensions, coated capsules, suppositories, lyophilized powders, transdermal patches or other forms known in the art. Various devices for metered drug delivery or sustained drug delivery may also be used.

Aqueous suspensions may contain the active ingredient in admixture with pharmacologically acceptable excipients, comprising suspending agents, such as methyl cellulose; and wetting agents, such as lecithin, lysolecithin or long-chain fatty alcohols. The said aqueous suspensions may also contain preservatives, coloring agents, flavoring agents, sweetening agents and the like in accordance with industry standards.

Parenteral preparations comprise particularly sterile or sterilized products. Injectable compositions may be provided containing the active compound and any of the well known injectable carriers. These may contain salts for regulating the osmotic pressure.

If desired, the compounds can be incorporated into liposomes by any of the reported methods of preparing liposomes for use in treating various conditions. The present compositions may utilize the compounds noted above incorporated in liposomes in order to direct these compounds to macrophages, monocytes, as well as other cells and tissues and organs which take up the liposomal composition. The liposome-incorporated compounds of the invention can be utilized by parenteral administration, to allow for the efficacious use of lower doses of the compounds. Ligands may also be incorporated to further focus the specificity of the liposomes.

Suitable conventional methods of liposome preparation include, but are not limited to, those disclosed by Bangham, A. D., et al., *J. Mol. Biol.* (1965) 23:238–252, Olson, F., et al., *Biochim. Biophys. Acta.* (1979) 557:9–23, Szoka, F., et al., *PNAS* (1978) 75:4194–4198, Kim, S., et al., *Biochim. Biophys. Acta.* (1983) 728:339:348, and Mayer, et al., *Biochim. Biophys. Acta.* (1986) 858:161–168.

As defined herein, an "effective amount" of a composition is that amount which produces a statistically significant effect. For example, an "effective amount" for therapeutic uses is the amount of the composition comprising an active compound herein required to provide a clinically significant decrease in symptoms of emphysema and/or hepatotoxicity.

For use in prophylactic context, effective amounts are those which succeed in preventing the onset of symptoms or minimizing the severity of such symptoms. Such effective amounts will be determined using routine optimization techniques and are dependent on the particular condition to be treated, the condition of the patient, the route of administration, the formulation, and the judgment of the practitioner and other factors evident to those skilled in the art. The dosage required for the compounds of the invention is manifested as an observed decrease in symptomology. General guidance for treatment regimens can also be obtained from experiments carried out in animal models of the disease of interest. See, also, Current Opinion in Structural Biology (1995) 5:605–611 for a review of studies on glycosylation inhibitors in biological systems.

Generally, the compounds of the invention can be administered to a typical human on a daily basis as an oral dose of about 1 mg/kg–1000 mg/kg, and more preferably from about 1 mg/kg to about 500 mg/kg. The parenteral dose will appropriately be 20–100% of the oral dose. While oral administration may be preferable in most instances (for reasons of ease, patient acceptability, and the like), alternative methods of administration may be appropriate for selected compounds and selected conditions.

EXAMPLES

The following examples are intended to illustrate but not limit the invention. A more detailed description of the experimental data is attached as Appendix A.

Preparation A

Production of Labeled α1-ATZ

The human fibroblast cell line CJZ12B which has been transduced with anthotropic recombinant retroviral particles to result in stable production of α1-ATZ mutant antitrypsin (Gross, V., et al., Biochem. J. (1986) supra) is used to produce α1-ATZ. The α1-ATZ mutant produced is labeled by adding 350–400 µCi TRAN$^{35}$S label to the medium.

Example 1

Effect of Glucosidase Inhibitors on Protein Molecular Weight

It has previously been shown that α1-ATZ mutant migrates at 52 kD in electrophoretic studies. It is believed this form is an intermediate with high mannose-type oligosaccharide side chains (Wu, Y., et al., PNAS (1994) supra). The α1-ATZ producing cell line of Preparation A was incubated for 1 hour in control serum-free medium or in serum-free medium supplemented with 100 µg/ml CST or 3 mM MDNJ. The cells were then labeled with TRAN$^{35}$S for 1.5 hours maintaining the presence of the drugs. The antitrypsin fraction was immunoprecipitated from the cell lysates, resolved by 10% SDS-PAGE and detected with the Phosphorimager system. In the presence of either drug, the precipitated α1-ATZ migrates more slowly, indicating the presence of additional sugars. The estimated molecular weight of the protein from treated cultures is 55 kD.

Example 2

Effect on Secretion

The procedure of Example 1 was repeated except that after the incubation with label, the cells producing α1-ATZ were "chased" for various time intervals still in the presence of drug. At these time intervals, extracellular fluid and cell lysates were clarified, immunoprecipitated and analyzed by 8–10% SDS PAGE as previously described. (Wu, Y., et al., PNAS (1994) supra).

In the absence of any drug, the 52 kD protein is retained for 1 hour in the cells, but begins to disappear from the cell lysate between 2–4 hours and only trace amounts of the 55 kD mature protein appear extracellularly.

In the presence of CST, the 55 kD protein disappears from the cell lysate at 2–4 hours but there is an increase in the 55 kD protein secreted into the medium and by 6 hours, 31% of the newly synthesized 55 kD protein was secreted into the medium. (Only 17% of α1-ATZ produced was secreted in the untreated control.)

In the presence of MDMJ, the disappearance of the 55 kD form from the cell lysate was accelerated over control, but there was no secretion of this "untrimmed" form. Similar results were obtained with the glucosidase inhibitor BDMJ.

Example 3

Effect of EST on ER Degradation

The data in the previous example demonstrated that the mutant α1-ATZ disappeared from the cell lysate at the same rate in the presence or absence of CST. However, an additional model system which has previously been shown to mimic the degradation of α1-ATZ in intact cells was employed to verify these results and expand them. This system was described by Qu, D., et al., J. Biol. Chem. (1996) 271:22791–22795 cited above. In general, reticulocyte lysate cell free system supplemented with canine pancreatic microsomes was programmed with purified α1-ATZ mRNA over 60 minutes at 30° C. The microsomes were then isolated by centrifugation and incubated in a proteolysis-primed lysate at 37° for various time intervals. Aliquots were taken and the samples resolved on 10% SDS-PAGE gels.

To test the effect of drug, the reaction mixture was pre-incubated for 10 minutes at 30° C. in the absence of CST or in the presence of 100 µg/ml CST. α1-ATZ mRNA and $^{35}$S-labeled methionine were added and translation conducted for 60 minutes at 30° C. in the absence or presence of CST. After co-translational translocation of α1-ATZ into the microsomes, the microsomes were harvested by centrifugation and the pellets suspended in 50 ml of proteolysis-primed lysate with or without CST. The samples were incubated at 37° C. and aliquots analyzed at various time intervals.

In the absence of drug, the 52 kD protein begins to disappear at 15–30 minutes and is completely degraded at 30–45 minutes. When CST is added as described, the 55 kD form begins to disappear after 30 minutes and disappearance is complete after 45–90 minutes. However, if the CST is not added at the pre-incubation phase, but rather during the chase period (i.e., after re-suspension of the microsomes), the 52 kD form showed the same disappearance rate as the control.

The procedure was repeated with 100 µg/ml CST present throughout and the microsomes were homogenized under nondenaturing conditions and immunoprecipitated with antibodies to calnexin and to a different chaperone, GRP78/BiP. The 52 kD form in the control was precipitated by anti-calnexin but the complex disappears between 30–45 minutes of the chase period. Little if any precipitate was formed with the microsomes incubated with CST. On the other hand, the 55 kD protein characteristic of the sample which includes CST is precipitated by anti-GRP78/BiP. This complex, too, disappears rapidly.

These data demonstrate that apparently the untrimmed α1-ATZ, present when CST is also present, is degraded rapidly by an alternate pathway involving an alternate chaperone. This alternate pathway is inhibited by the proteasomal inhibitor MG132. However, it is estimated that only 5–10% of the total α1-ATZ is co-precipitated with the anti-GRP78/BiP antibody.

Example 4

Effect of Mannosidase Inhibitors

The effect of the mannosidase inhibitors KIF (mannosidase I), DMJ (mannosidase I and II) and an additional inhibitor, DIM (mannosidase II) on electrophoretic mobility was tested as described in Example 1. The results showed that DMJ and KIF resulted in somewhat slower migration as compared to the 52 kD "trimmed" form.

Example 5

Effect of Mannosidase Inhibitors on Secretion

The pulse-chase experiments of Example 2 were repeated with the mannosidase inhibitors DMJ (1 mM) KIF (0.3 mM) and DIM (1 mM). In the presence of DMJ or KIF, the intracellular and secreted protein both have molecular weights of 52 kD. While the protein is retained intracellularly for a longer period of time in the treated cells than in control, there is an increase in the amount of secreted protein. The half-life for disappearance of α1-ATZ from the lysate in the control is 0.95 hours and the fraction secreted is 0.11. In the presence of KIF, however, the half-life for disappearance from the lysate is 2.78 hours and the fraction secreted is 0.31; in the presence of DMJ, the half-life in the lysate is 2.12 hours and the fraction secreted is 0.28. (Control values were slightly different in this latter experiment.) There was no effect of DIM on degradation or secretion.

Example 6

Characterization of Carbohydrate Side Chains

Wild type α1-AT is secreted from HepG2 cells with a molecular weight of 55 kD. It is resistant to digestion with endoH but is cleaved to a 46 kD polypeptide by PNGaseF.

EndoH is glycolytic only for high mannose and complex carbohydrate glycosylation chains; PNGaseF cleaves any carbohydrate and would be expected to degrade the glycosylation side chains of any glycoprotein.

The product of CST-treated recombinant CJZ 12B cells, which secrete the mutant α1-ATZ of 55 kD show partial sensitivity to endoH. Treatment with this enzyme results in a mixture of peptides of molecular weights 46 kD, 48 kD, and 52 kD. This 55 kD α1-ATZ polypeptide was cleaved to 46 kD by PNGaseF.

The peptide secreted by KIF treated CJZ12B cells was cleaved both by endoH and PNGaseF to a 46 kD product.

Example 7

Activity of Secreted α1-ATZ

Both HepG2 cells, secreting wild type antitrypsin, and CJZ12B cells, which secrete the mutant, were subjected to pulse-chase conditions as described, for example, in Example 2. The mutant-secreting cells were treated with KIF (0.3 mM) DMJ (1 nM) or CST (100 μg/ml). The extracellular media from the 6 hours time point of the chase period were harvested and then incubated for 30 minutes at 37° with neutrophil elastase at various concentrations. The reaction mixtures were then immunoprecipitated with anti-antitrypsin and resolved by SDS PAGE.

Wild type antitrypsin forms high molecular weight complexes with the elastase of molecular weight 66 kD and 75 kD and complexes begin to form at 0.1 μg elastase. Conversion is complete by 0.5 μg elastase.

The mutant α1-ATZ of 55 kD from CST-treated cells also forms complexes at 75 kD which become apparent at 0.5 μg elastase and complete conversion requires 2 μg elastase.

The mutant 52 kD antitrypsin from KIF or DMJ treated cells form 70 kD complexes which start to form at 0.5 μg elastase and are complete at 2 μg elastase.

What is claimed is:

1. A method to treat, therapeutically or prophylactically, conditions associated with α1-antitrypsin deficiency in a subject characterized by the presence of mutant α1-ATZ antitrypsin, which method comprises administering to said subject an effective amount of a glucosidase inhibitor or of an imino sugar or reduced imino sugar.

2. The method of claim 1 wherein the glucosidase inhibitor is castanospermine (CST) or a structural analog thereof.

3. The method of claim 1 wherein said glucosidase inhibitor is CST.

4. A method to treat, prophylactically or therapeutically, a condition of emphysema in a subject, wherein said subject is characterized by the presence of mutant α1-ATZ antitrypsin, which method comprises administering to said subject an effective amount of a glucosidase inhibitor or a mannosidase I inhibitor or of an imino sugar or reduced imino sugar.

5. A method to treat, prophylactically or therapeutically, a condition of liver damage in a subject, wherein said subject is characterized by the presence of mutant α1-ATZ antitrypsin, which method comprises administering to said subject an effective amount of a glucosidase inhibitor or of an imino sugar or reduced imino sugar.

6. A method to treat, therapeutically or prophylactically, conditions associated with α1-antitrypsin deficiency in a subject characterized by the presence of mutant α1-ATZ antitrypsin, which method comprises administering to said subject an effective amount of 4-phenylbutyric acid.

* * * * *